(12) United States Patent
Mannhardt et al.

(10) Patent No.: US 7,869,028 B2
(45) Date of Patent: Jan. 11, 2011

(54) APPARATUS FOR THE ELECTROMAGNETIC SPECTRUM OR OPTICAL ANALYSIS, IN PARTICULAR PHOTOMETRIC, SPECTROPHOTOMETRIC OR IMAGE ANALYSIS

(75) Inventors: Joachim Mannhardt, Heergasse 3, Eschach (DE) 73569; Trevor Page, Bellapais, Lime Walk, Dibden Purlieu, Southampton (GB) SO 454 RA

(73) Assignees: Joachim Mannhardt, Eschach (DE); Trevor Page, Southampton (GB)

( * ) Notice: Subject to any disclaimer, the term of this patent is extended or adjusted under 35 U.S.C. 154(b) by 385 days.

(21) Appl. No.: 11/995,403

(22) PCT Filed: May 12, 2006

(86) PCT No.: PCT/EP2006/004496

§ 371 (c)(1),
(2), (4) Date: Jan. 11, 2008

(87) PCT Pub. No.: WO2007/009522

PCT Pub. Date: Jan. 25, 2007

(65) Prior Publication Data

US 2008/0212087 A1    Sep. 4, 2008

(30) Foreign Application Priority Data

Jul. 15, 2005    (DE) .................. 20 2005 011 177 U

(51) Int. Cl.
*G01N 1/10* (2006.01)
*G01N 21/00* (2006.01)

(52) U.S. Cl. ...................... 356/246; 356/432
(58) Field of Classification Search ........................ None
See application file for complete search history.

(56) References Cited

U.S. PATENT DOCUMENTS

| | | |
|---|---|---|
| 4,561,779 A | 12/1985 | Nagamune et al. |
| 4,759,958 A | 7/1988 | Numata et al. |
| 4,914,310 A | 4/1990 | Jarofski |
| 5,366,801 A | 11/1994 | Bryant et al. |
| 5,453,832 A | 9/1995 | Joyce et al. |
| 5,510,895 A | 4/1996 | Sahagen |
| 5,591,907 A | 1/1997 | Stein et al. |
| 5,605,841 A | 2/1997 | Johnsen et al. |
| 6,058,776 A | 5/2000 | Algers et al. |
| 6,175,676 B1 | 1/2001 | Sharan |
| 6,873,409 B1 | 3/2005 | Slater |
| 7,382,458 B2 * | 6/2008 | Johnson et al. ............. 356/436 |

* cited by examiner

*Primary Examiner*—Gregory J Toatley
*Assistant Examiner*—Amanda H Merlino
(74) *Attorney, Agent, or Firm*—Harvey S. Kauget; Phelps Dunbar LLP

(57) ABSTRACT

An apparatus for the electromagnetic spectrum or optical analysis of a material. The apparatus comprising a measuring probe having a housing with at least one radiation or light measuring element, a measuring window and with at least one detection element for the analysis. The measuring probe is formed and guided displaceably in the axial direction in such a way that at least part of the housing in which the measuring window is located enters through an opening in which the material to be analyzed is located for the analysis. The at least one measuring window is arranged in at least one subregion of the circumferential wall of the housing. A sealing cap is located between a front end face of the housing and the measuring window arranged in the circumferential wall and consequently covers the opening in a retracted position of the measuring probe.

50 Claims, 4 Drawing Sheets

APPARATUS FOR THE ELECTROMAGNETIC SPECTRUM OR OPTICAL ANALYSIS, IN PARTICULAR PHOTOMETRIC, SPECTROPHOTOMETRIC OR IMAGE ANALYSIS

The invention relates to an apparatus for the electromagnetic spectrum or optical analysis of a material to be analyzed that is located in a product space, such as a container or tube, in particular for the photometric, spectrophotometric or image analysis of powder, bulk material, granules and the like, with a measuring probe which is arranged in a housing, with at least one radiation or light measuring element, a measuring window which is arranged in the path of rays in a wall of the housing, and with at least one detection element for the analysis, the measuring probe being formed and guided displaceably in the axial direction in such a way that at least part of the housing in which the measuring window is located enters through an opening into the product space in which the material to be analyzed is located, for the analysis. The invention also relates to a method for the analysis of a material to be analyzed that is located in a product space.

It is known from U.S. Pat. No. 6,873,409 B1 to analyze the composition, density, moisture content and the like of a material to be analyzed by photometric or spectrophotometric analysis in reflection or transreflection by means of a measuring probe which is introduced into the interior of a container with said material. Areas of use for this are for example mixers, dryers, granulating devices, reactors, sprayers, coaters and the like, in particular in the pharmaceuticals industry. According to the prior art, the measuring probe with its measuring and detection elements arranged in a housing has a measuring window which is arranged at the extreme front end of the measuring probe or the housing of the measuring probe. Light consequently radiates in the axial direction, in the direction of the probe. There, light is reflected at particles, for example, and light that is not absorbed is reflected back to the measuring probe.

Also known is the use of an integration sphere, known as an Ulbricht sphere, for analysis purposes. The Ulbricht sphere is used for spectral reflection measurement on solid or liquid specimens. This involves light of a light source being passed by an optical quartz glass window into the Ulbricht sphere. The specimen to be measured is diffusely illuminated and the total reflection measured, or directly illuminated and a diffuse reflection detected. The reflected light is directed via a further glass fibre to a fibre-optic spectrometer for a spectral evaluation. The Ulbricht sphere itself is a hollow sphere, the inside surface of which consists of a diffusely and highly reflective material. By multiple reflection within the sphere, the sphere operates either as an emitter or a detector with a Lambert characteristic.

In the case of known arrangements, measurement is carried out during the process through a measuring window. However, this involves the problem that, depending on the material to be analyzed, the measuring window very quickly becomes soiled or covered with particles from the process or mists up. Cleaning of the measuring probe located inside the container is extremely difficult, in some cases even impossible. If a measuring probe which enters an opening of the container and measures axially in the longitudinal direction of the measuring probe is used, the measuring window can only be cleaned by removing or uninstalling the measuring probe, or alternatively by flushing being carried out after the production process if the measuring probe remains inside the container. Cleaning during the process is not possible without disrupting it.

As further prior art, reference is made to U.S. Pat. No. 6,058,776 and U.S. Pat. No. 5,591,907.

The present invention is based on the object of providing a measuring probe of the type mentioned at the beginning which allows the probe, in particular the measuring window or windows, to be cleaned in a simple way even during the production process.

According to the invention, this object is achieved by at least one measuring window being arranged in at least one subregion of the circumferential wall of the housing, and by a sealing cap being located between a front end face of the housing and the measuring window arranged in the circumferential wall, which sealing cap is at least partially still in the region of the 2-0 opening in the product space, and consequently covers the opening, in a retracted position of the measuring probe in which the measuring window is outside the product space.

The arrangement of the measuring window in the circumferential wall and the sealing cap arranged according to the invention have the effect that it is merely necessary to retract the housing with the measuring probe from the opening of the container through which the housing with the measuring probe is pushed to the extent that the measuring window is outside the product space, but at the same time the sealing cap is still inside, and in this way seals the opening. In this position, it is then possible in an advantageous way for the measuring window to be cleaned without any problem, to be precise without the process that is taking place in the product space being disrupted, if the sealing cap forms a corresponding seal with respect to the interior of the product space. Subsequently, the housing with the measuring probe with its measuring and detection elements can be lowered again through the opening into the interior of the product space, after which further measurements and analyses can be carried out.

In a very advantageous refinement of the invention, it may be provided that a flushing device for cleaning at least the measuring window of the measuring probe in the retracted position of the measuring probe is provided.

The flushing device according to the invention allows the housing of the measuring probe, in particular the region with the measuring window, to be cleaned.

In a form of construction for this, it may be provided that the flushing device has a flushing medium chamber, which is arranged in an intermediate space between the housing and a guide at least in the region of the measuring window, the flushing medium chamber being provided with at least one inflow and at least one outflow for flushing medium.

In a further advantageous refinement, it may be provided that the guide is provided with at least one gas connection for feeding dry gas into the interior of the cylinder guide. The dry gas can be used for drying the exterior of the housing, in particular the region with the measuring window, after its cleaning, before the measuring probe is reintroduced into the interior of the product space.

In a development, it may also be provided that the gas pressure in the interior of the guide is checked by a gas pressure testing device. In this way, leakages both to the outside and into the interior of the product space can be established. In particular, in this way the functionality of a sealing part between the measuring probe or the housing of the measuring probe and the container or the closed guide, for example a cylinder guide, can be checked.

In a very advantageous refinement according to the invention, it may be provided that, with axial feeding of the radiation or the light in the interior of the housing, at least one beam deflecting device is provided, which brings about a deflection of the beam or light in a radial direction, in order that the material to be analyzed is correspondingly irradiated via the measuring window arranged in the circumferential wall and reflected rays are detected again through the window and subsequently, after renewed deflection, can be led out again from the measuring probe for analysis or evaluation.

A wide variety of devices are possible as the beam deflecting device. In a simple way, one or more mirrors may be provided for this purpose, distributed over the circumference, arranged and formed in a way dependent on the circumferential length of the measuring window or windows. Similarly, formation as a pyramid or a cone or truncated cone is also possible. In this way, a number of mirrors surfaces are obtained. If a four-, six- or eight-sided pyramid is used, the possibilities of performing a number of measurements or analyses with different parameters in conjunction with a corresponding number of measuring windows are obtained as a further advantage. For this purpose, it is then merely necessary also to provide a corresponding number of detection elements, such as for example receiving light guides.

A further considerable advantage of the way in which the measuring probe is formed according to the invention, and the way in which the measuring window is arranged, is that it is consequently also possible to carry out a referencing, for example a white balance or some other calibrations, during the measurement. For this purpose, it is merely necessary to move the housing with the measuring probe partially out of the product space by a corresponding amount, after which corresponding calibrations or reference measurements can be carried out through the measuring window by reference and/or test elements arranged in a guide for the housing.

In addition, the apparatus according to the invention also allows the arrangement of various transmitting and receiving light guides in different measuring arrangements and their use with different measuring methods.

In addition, in this way there is the possibility of carrying out functional checks without the measuring probe having to be uninstalled.

With the apparatus according to the invention, virtually all know measuring methods can be carried out by a corresponding arrangement of light guides, such as for example reflection/remission or transreflection (UV, VIS, NIR, IR), fluorescence or laser induced fluorescence (LIF), bio- or chemiluminescence or Raman spectroscopy. Similarly, a laser induced breakdown spectroscopy (LIBS) or two-beam arrangement with return of the reference signal is possible.

In addition, the apparatus according to the invention can also be used for temperature measurement, if for example a temperature measuring element which is connected to the measuring probe or the receiving detectors is arranged in the sealing cap. In this way, temperature measurements are also possible in the product space for the specimen material.

In the measuring probe itself, a wide variety of transmitting and detecting elements and arrangements may be accommodated. In this respect, the transmitting/detecting elements may be similar or different, to allow different analyses to be carried out.

In a further refinement of the invention, it may also be provided that the beam deflecting device, for example a mirror body, is turned or pivoted during the application. In this way it is possible for example for a greater area to be covered in the container.

A further advantage of the apparatus according to the invention is that, depending on its length, the measuring probe can also be introduced to any desired length into the container with the product located in it. In this way it is possible by measurements at different depths of entry for a corresponding profile of the total contents to be obtained. With measurements at different depths, it is possible for example for mixing, drying, granulating and coating processes to be monitored and/or analyzed even better.

In addition, it is also possible through the measuring window or windows not only to carry out an all-round measurement of 360°, but also to perform segmental measurements. For example, in the case of a homogeneous distribution of the specimen, a characteristic feature of the product being analyzed can be measured over one segment at a specific wavelength, while another property of the product is measured or analyzed over another segmental region, possibly at a different wavelength. Similarly, it is possible for example to work in one segmental region with visible light, in order to measure the color, while for example the fluorescence or NIR (near infrared) is measured in another segmental region. This means that it is possible to work with the same or different measuring methods in the individual segmental regions to be measured that are formed by the measuring windows, and to do so in one operation, or with a single insertion of the measuring probe into the product space.

Exemplary embodiments of the invention are described in principle below on the basis of the drawing, in which.

Figure 1:
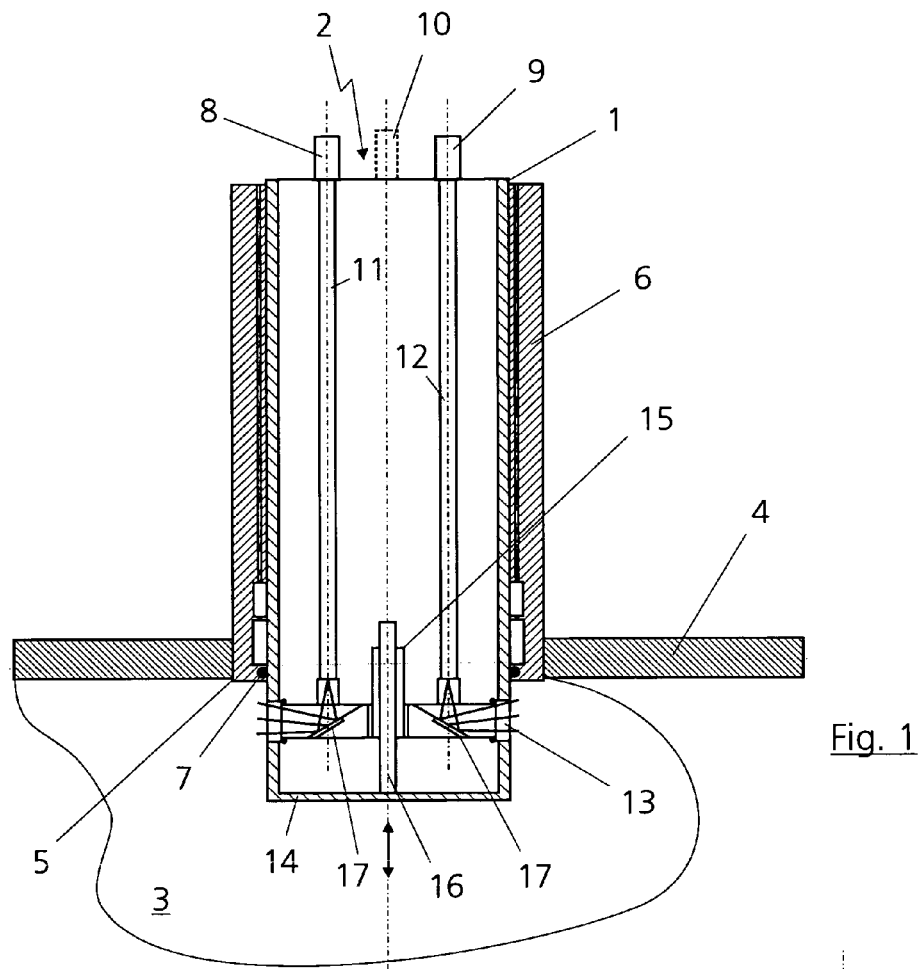
FIG. 1 shows the apparatus according to the invention in section with part of the container.

The apparatus represented in FIG. 1 has a measuring probe 2 with a housing 1, which are provided with various devices for the electromagnetic spectrum or optical analysis of material to be analyzed that is located in a product space, for example a container 3. In this respect, the term "optical analysis" refers also to the use of non-visible light. Of the container 3, only a detail and part of its wall 4 with an opening 5 are represented. Instead of a container 3, a tube or a tube-like vessel or any other form may also be provided as the product space. The opening 5 is sealed with respect to the outside by a guide, for example a closed cylinder guide 6, and a sealing ring 7, which is arranged in the front end wall of the cylinder guide 6. The cylinder guide 6 at the same time also represents a guide for the housing 1, and consequently for the measuring probe 2. The housing 1 and the cylinder guide 6 are cylindrically formed and the measuring probe 2 is displaceable together with the housing 1 in the axial direction with respect to the cylinder guide 6, whereby it can be introduced into the interior of the container 3.

In principle, the construction of the measuring probe 2 is of a known type, for which reason only the parts that are important for the invention are described in more detail below.

In FIG. 1, a connection 8 for a transmitting light guide and a connection 9 for a receiving light guide are represented. In addition, if need be, a connection 10 for a temperature sensor may also be provided. The connections 8, 9 and 10 are connected in a known way to a testing and evaluation unit (not represented).

Arranged in the interior of the measuring probe 2 are, for example, a number of transmitting light guides 11, arranged distributed over the circumference, and one or more receiving light guides 12. In this case, each light guide may if need be also comprise a combination of a number of light guides or be a bundle of light guides, in order to carry out the various known measuring methods, such as for example Raman, fluorescence, LIF or LIBS. Depending on the design of the light guides, various combinations of measuring methods with different light guide configurations may also be carried out, such as for example measurements in reflection and fluorescence measurements. If appropriate, for this purpose the associated light guides are coupled to corresponding detectors (not represented).

In the front region of the housing 1 of the measuring probe 2, entering the container 3, one or more measuring windows 13 are arranged in the circumferential wall of the housing 1. If the measuring window 13 extends in an annular form over the entire circumference of the housing 1, 3600 measurements are possible. To be used as the material for the measuring window or windows 13 is a material which is resistant to aggressive media, such as for example sapphire or quartz. For an end termination of the housing 1, the measuring window or windows 13 is or are adjoined by a sealing cap 14, which is connected with a sealing effect to the measuring window or windows 13 and to the rest of the housing 1 in a way not represented in any more detail, in order that sealing with respect to the interior of the measuring probe 2 is produced. A central screwed connection 15 (not represented in any more detail) with sealing elements may be provided for example as the fastening. If need be, a temperature sensor 16 may also be arranged in the sealing cap 14, in order to measure the temperature in the interior of the container 3 with the material to be analyzed.

For the deflection of the rays generated by the transmitting light guide or guides 11, a radiation deflecting device in the form of deflecting mirrors 17 is arranged in the region of the measuring window or windows 13. The deflecting mirrors 17 may be aligned for example in such a way that they are distributed over the circumference at an angle 45° to the longitudinal axis of the measuring probe 2 and of the housing 1, in order that the axially incident rays are deflected in a radial direction and in this way can emerge radially from the measuring window or windows 13, and consequently the material to be analyzed can be analyzed correspondingly. The deflecting mirrors 17 also serve at the same time for deflecting radiations reflected in the interior of the container and further measured values, which are returned via the receiving light guide or guides 12 to the evaluation unit (not represented).

Figure 7:
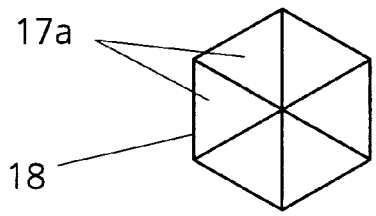
FIG. 7 shows a plan view of a beam deflecting device in the form of a pyramid.

Instead of a number of mirrors arranged distributed over the circumference, a mirror unit in the form of a cone, the form of a truncated cone or the form of a pyramid may also be used, corresponding mirror surfaces 17a being provided, as represented for example in the plan view of a pyramid 18 according to FIG. 7. If a number of measuring windows 13 or a measuring window 13 which extends over 360° is or are used, a combination of different measuring methods can be carried out in conjunction with a number of mirrors 17 or mirror surfaces 17a, if a corresponding number of receiving light guides 12 are provided.

Figures 2, 3:
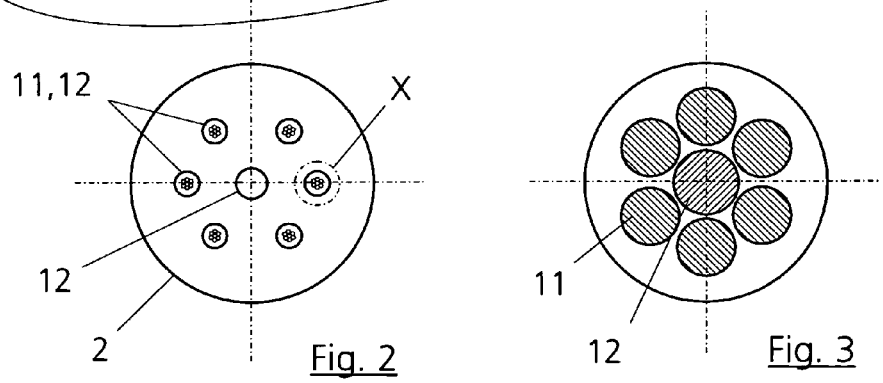
FIG. 2 shows a cross section through the measuring probe.
FIG. 3 shows an enlarged representation of a transmitting/receiving light guide unit according to detail "X" of FIG. 2.

The central measuring element represented in FIG. 2 may represent a transmission light guide or receiving light guide 12 or in each case a multiplicity of them. The same applies to the transmitting light guides 11 arranged distributed over the circumference, six for example, which may likewise comprise a combination of transmitting light guides 11 and receiving light guides 12.

Shown for example in this respect in FIG. 3 is an enlarged representation of such an individual unit according to the enlargement of detail "X" in FIG. 2, likewise comprising for example six transmitting light guides 11 and one central receiving light guide 12. Here, too, a wide variety of combinations are possible. Similarly, a uniform arrangement and distribution of transmitting light guides 11 and receiving light guides 12 is possible. The same also applies to a different distribution of the total of seven units that are represented in FIG. 2.

Figure 4:
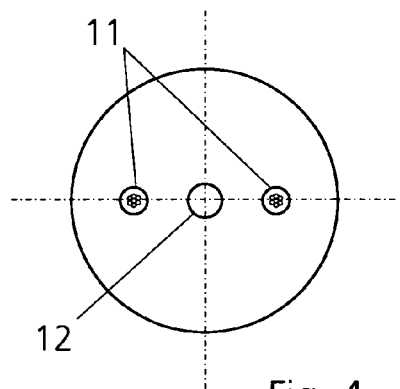
FIG. 4 shows a cross section through the measuring probe with another arrangement of transmitting and receiving light guide units.

In FIG. 4 there is shown a simple design of a measuring probe 2 with a central receiving light guide 12 and two transmitting light guides 11 arranged diametrically opposite. The two diametrically opposite light guides may likewise have in each case a number of transmitting light guides 11 and receiving light guides 12.

Figure 5:
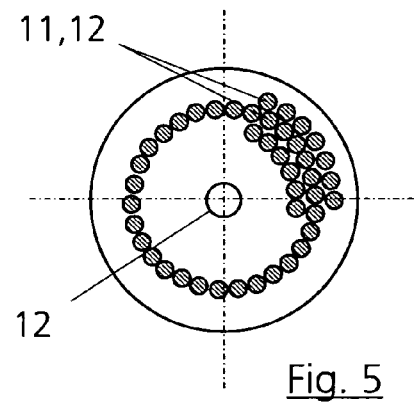
FIG. 5 shows a further cross section through the measuring probe with a multiplicity of transmitting/receiving light guide units.

FIG. 5 shows a design with a multiplicity of transmitting light guides 11 and receiving light guides 12. As can be seen, the transmitting and receiving light guides 11, 12 may be arranged alternately in a ring or—as represented—in a number of rings, or else alternating in a row.

If appropriate, the number of transmitting light guides 11 may also outweigh the number of receiving light guides 12, in order to ensure adequate illumination of a measuring area.

The housing 1 with the measuring probe 2 may enter the interior of the container 3 steplessly or in increments. FIG. 1 shows the position of the measuring probe 2 during the measuring methods, while FIG. 6 represents a position in which the measuring probe 2 is located in a pushed-in position, in which cleaning of the measuring windows 13 takes place by a flushing device 19 (not represented in any more detail), from which flushing medium is introduced into the region of the measuring windows 13 and also discharged again from them via one or more channels 20 arranged in the cylinder guide 6.

Figure 6:
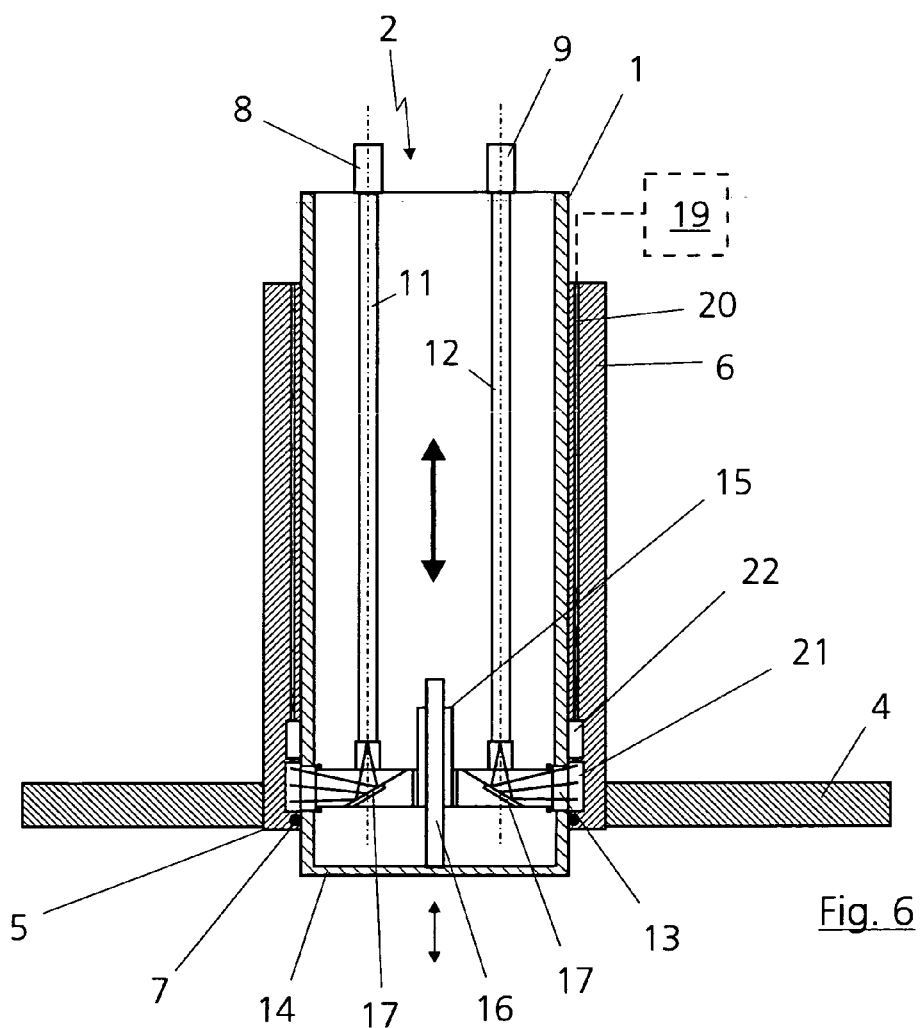
FIG. 6 shows the device as shown in FIG. 1 with a retracted or pushed-back housing with the measuring probe in a measuring/reference and cleaning position for the measuring window.

As can be seen from comparing FIGS. 1 and 6, the cleaning of the measuring window or windows 13 may also be carried out during the normally proceeding course of the process, since sealing of the opening 5 continues to be effected by the sealing cap 14 arranged on the end face of the housing 1 in conjunction with the sealing ring 7 as a sealing element. On the other hand, as a result, the region of the measuring window or windows 13 is outside the container 3 and can in this way be cleaned.

At the same time, in the position according to FIG. 6 it is possible if need be also to carry out further measuring methods with specific reference material, for example by a white balancing device 21. For this purpose, a white standard calibration element may be provided for example, an identical or different sensor in a second calibration position performing a comparison with a black standard calibration element. Similarly, it is also possible with a calibrating device 22, which is correspondingly not represented in any more detail and, in a way similar to the white balancing device 21, is arranged in the cylinder guide 6, to carry out calibrating operations that are not explained in any more detail. In principle, however, such measuring methods and calibrating operations are generally known.

Figure 8:
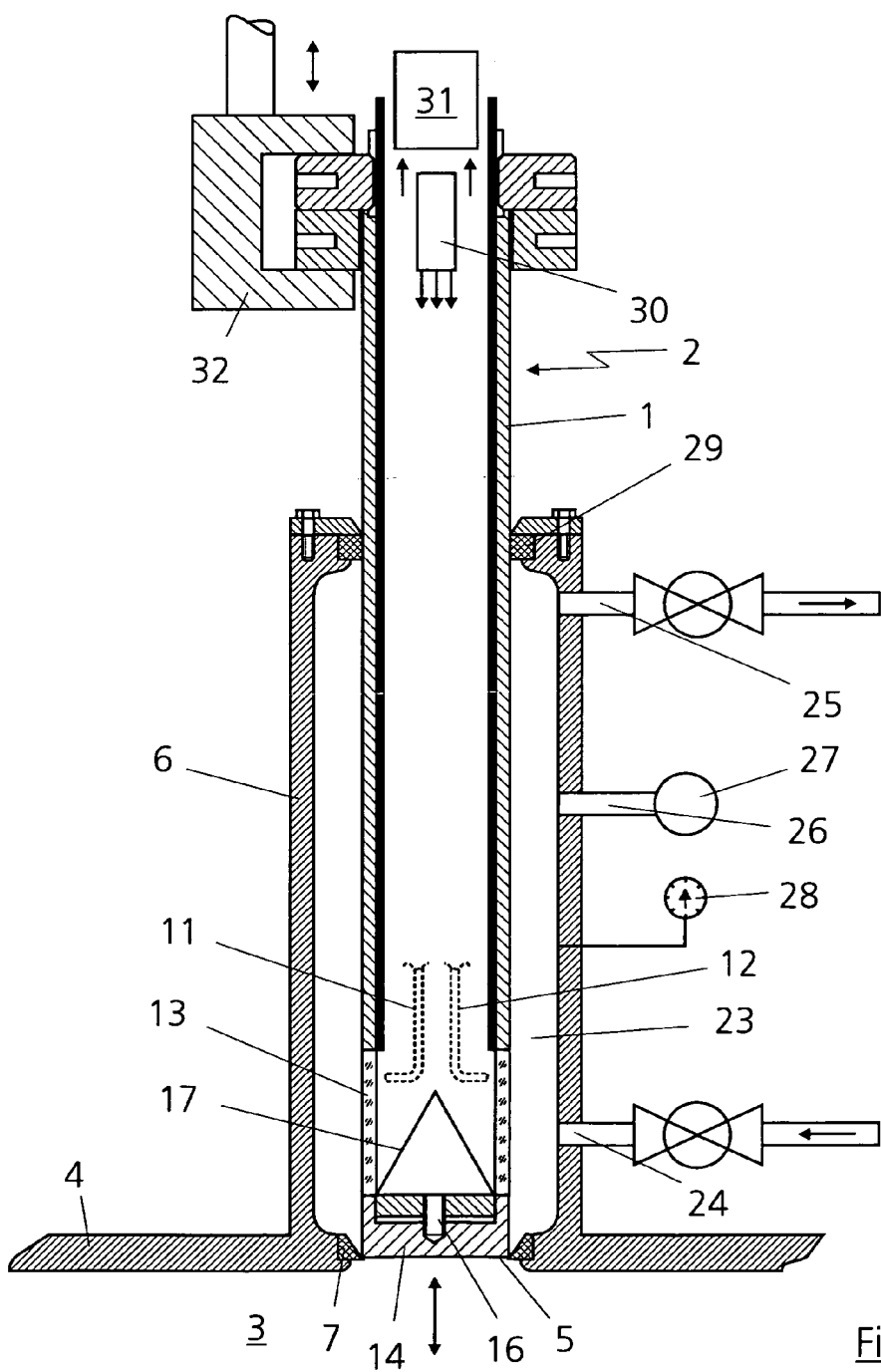
FIG. 8 shows an apparatus according to the invention, similar to the apparatus shown in FIG. 1, with representation of a cleaning system.

The apparatus represented in longitudinal section in FIG. 8 is in principle of the same construction as the apparatus described above. For this reason, the same reference numerals have also been retained for the same parts.

In FIG. 8, the cleaning system is represented in more detail in the state it assumes in the retracted position of the measuring probe 2, corresponding to FIG. 6. As can be seen, apart from its sealing function, the sealing part 7, which is arranged in the container 4 in the cylinder guide 6 and circumferentially bounds the opening 5, in this case also represents a scraper ring. Product from the interior of the container that adheres to the outer wall of the housing 1 is in this way scraped off at the sealing part 7, formed as a scraper ring, during the retraction of the measuring probe 2.

As can be seen, in this position the measuring window 13 is outside the container 3. Between the housing 1 of the measuring probe 2 and the inner wall of the cylinder guide 6 there is an intermediate space 23. The cylinder guide 6 is provided with an inflow 24 and a return 25 for flushing medium, the openings of the inflow 24 and of the return 25 protruding into the cylinder space 23. Flushing medium, for example flushing liquid, is fed, preferably under pressure, from a flushing device via the inflow 24 (see also FIG. 6), whereby the window surface of the measuring window 13 can be cleaned.

In addition, the intermediate space 23 may be connected via a pressure connection 26 to a compressed air source 27. By additionally feeding compressed air into the intermediate space 23, drying can be achieved after cleaning of the measuring window 13 and the remaining area of the housing 1. If, in addition, there is also a connection to a gas pressure testing device 28, a pressure test of the intermediate space 23 for the integrity of the seal between the sealing part 7 and a rear seal 29 can also be achieved at the same time as the drying.

From FIG. 8 there can also be seen in principle a light source 30, which is connected to the transmitting light guides 11, represented in principle in FIGS. 1 and 6.

A fibre-optic collector 31 may be provided for receiving the light or the rays returned via the receiving light guides 12.

Instead of a beam deflecting device, for example the deflecting mirror 17 represented, the transmitting light guides 11 and the receiving light guides 12 may also be deflected from their axial directions into a radial direction, or obliquely, in their lower regions, i.e. in the region of the measuring window 13, that direct further transmission of the rays or the light and also direct reception take place (see representation in dashed lines respectively of a transmitting light guide and a receiving light guide).

Also represented in FIG. 8 is an actuator 32, by means of which the measuring probe 2 can be introduced into the container 3 and also partially or fully removed again from it.

It goes without saying that it is also possible to carry out still further testing and measuring methods in the retracted position without disrupting the normal operation of the process. The same also applies to further cleaning and/or repair operations on the housing 1 or in or on the measuring probe 2 and its individual parts.

Figure 9:
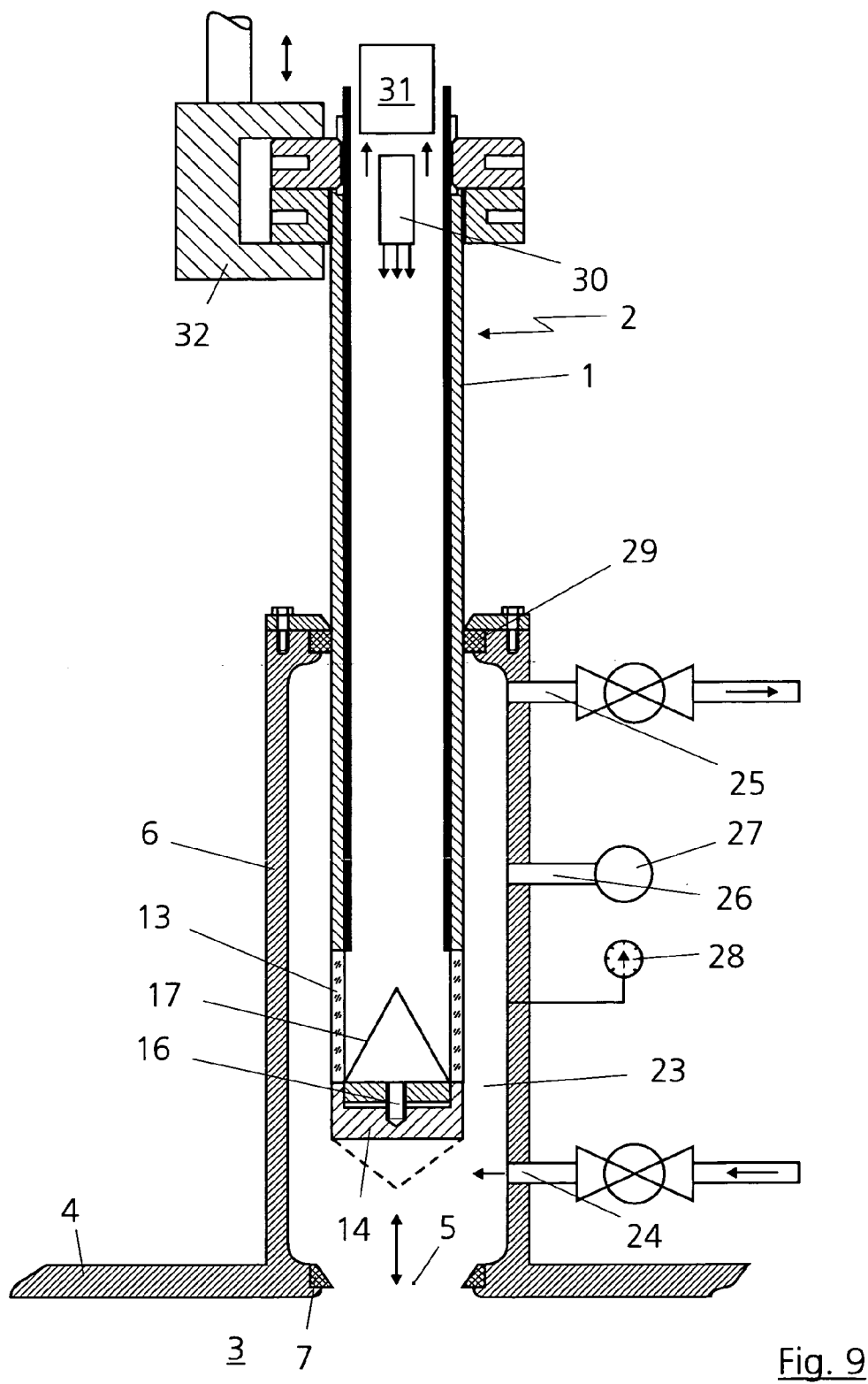
FIG. 9 shows an apparatus corresponding to the apparatus as shown in FIG. 8, the measuring probe being retracted even further.

For example, it may be provided that the measuring probe 2 together with the housing 1 is retracted still further by the actuator 32, as represented in FIG. 9.

It can be seen that in this way the opening 5 in the interior of the container 3 can consequently be uncovered and the sealing cap 14 is located in the region of the inflow 24 in the intermediate space 23, through which the flushing takes place. In this position, the sealing cap 14 can consequently also be cleaned on its circumferential wall and also its underside. In the same way, it is also possible to flush or clean the interior of the container 3. For this purpose, it may also be provided that the underside of the sealing cap 14, which is directed toward the interior of the container, is formed such that it is rounded or even in the form of a cone (see representation in dashed lines in FIG. 9). In this way there is a deflection of the jet of flushing medium, and consequently better introduction into the interior of the container 3. Furthermore, on its side facing the sealing part 7, the hosing 1 can be provided with a chamfer, thereby providing a small gap between the sealing part 7 and the hosing 1, which provides a higher velocity of the cleaning fluid an thereby a better cleaning result. For this purpose, also the cone described above can be used. It goes without saying that the cylinder guide 6 does not have to be circularly formed, but if need be may also have—seen in cross section—an oval, polygonal or any other form.

Consequently, in the retracted position of the measuring probe 2, system tests can be performed in compliance with generally known test standards. Apart from calibration, system checks are consequently also possible and, apart from cleaning, drying of the measuring probe 2 or the housing 1 is also possible.

The apparatus described above is also useful for particle size measurement, in particular for optical particle size measurement.

The invention claimed is:

1. An apparatus for the electromagnetic spectrum or optical analysis of a material to be analyzed that is located in a product space for the photometric, spectrophotometric or image analysis of powder, bulk material, and granules, with a measuring probe which is arranged in a housing, with at least one radiation or light measuring element, a measuring window which is arranged in a path of rays in a wall of the housing, and with at least one detection element for the analysis, the measuring probe being formed and guided displaceably in a guide in an axial direction in such a way that at least part of the housing in which the measuring window is located enters through an opening into the product space in which the material to be analyzed is located, for the analysis, wherein at least one measuring window is arranged in at least one sub-region of a circumferential wall of the housing, and that the same measuring window is used in reflection for the detection element, and a sealing cap is located between a front end face of the housing and the measuring window arranged in the circumferential wall, which sealing cap is at least partially still in the region of the opening in the product space, and consequently covers the opening, in a retracted position of the measuring probe in which the measuring window is outside the product space, wherein reference and/or test elements are arranged in the guide.

2. The apparatus as claimed in claim 1, wherein the guide is a cylinder guide, which can be positioned in the opening of the product space or which forms part of the product space.

3. The apparatus as claimed in claim 2, wherein the guide is provided with a sealing part, which interacts with the measuring window and/or the sealing cap of the housing.

4. The apparatus as claimed in claim 3, wherein the sealing part is formed as a scraper ring.

5. The apparatus as claimed in claim 1, wherein at least one reference element for a white standard is provided.

6. The apparatus as claimed in claim 5, wherein, as test elements, at least one calibrating device is provided.

7. The apparatus as claimed in claim 1, wherein, as a measuring element, at least one transmitting light guide is provided.

8. The apparatus as claimed in claim 1, wherein, as a detection element, at least one receiving light guide is provided.

9. The apparatus as claimed in claim 8, wherein a bundle of receiving light guides is provided.

10. The apparatus as claimed in claim 1, wherein axially fed transmitting and receiving light guides are respectively deflected at least approximately in a radial direction toward the measuring window in their front region, facing the product space.

11. The apparatus as claimed in claim 1, wherein the measuring probe arranged in the housing is formed in a cylinder guide such that it can enter the interior of the container steplessly or in increments.

12. The apparatus as claimed in claim 11, wherein analyses can be carried out with the measuring probe in each case at different depths of entry into the interior of the product space.

13. The apparatus as claimed in claim 1, wherein the measuring window is formed from sapphire or quartz.

14. The apparatus as claimed in claim 1, wherein a number of measuring windows are arranged distributed over the circumferential wall of the housing.

15. The apparatus as claimed in claim 14, wherein analyses can be carried out segmentally through the measuring windows.

16. The apparatus as claimed in claim 15, wherein the segmental analyses can be carried out on the basis of same or different measuring methods.

17. The apparatus as claimed in claim 1, wherein the measuring probe is provided with a temperature measuring element.

18. An apparatus for the electromagnetic spectrum or optical analysis of a material to be analyzed that is located in a product space for the photometric, spectrophotometric or image analysis of powder, bulk material, and granules, with a measuring probe which is arranged in a housing, with at least one radiation or light measuring element, a measuring window which is arranged in a path of rays in a wall of the housing, and with at least one detection element for the analysis, the measuring probe being formed and guided displaceably in a guide in an axial direction in such a way that at least part of the housing in which the measuring window is located enters through an opening into the product space in which the material to be analyzed is located, for the analysis, wherein at least one measuring window is arranged in at least one subregion of a circumferential wall of the housing, and that the same measuring window is used in reflection for the detection element, and in that a sealing cap is located between a front end face of the housing and the measuring window arranged in the circumferential wall, which sealing cap is at least partially still in the region of the opening in the product space, and consequently covers the opening, in a retracted position of the measuring probe in which the measuring window is outside the product space, wherein reference and/or test elements are arranged in the guide and that a flushing device for cleaning at least the measuring window of the measuring probe in the retracted position of the measuring probe is provided, wherein the flushing device has a flushing medium chamber, which is arranged in an intermediate space between the housing and the guide at least in the region of the measuring window, the flushing medium chamber being provided with at least one inflow and at least one outflow for flushing medium.

19. The apparatus as claimed in claim 18, wherein, for cleaning the sealing cap or the interior of the product space, the measuring probe can be pushed into a position in which there is a connection between the flushing medium chamber and the product space.

20. The apparatus as claimed in claim 18, wherein the guide is provided with at least one gas connection for feeding dry gas into the interior of a cylinder guide.

21. The apparatus as claimed in claim 20, wherein the guide is provided with a gas pressure testing device for gas pressure testing for the interior of the guide.

22. The apparatus as claimed in claim 18, wherein between the housing and the inner wall of the guide an intermediate space is arranged, wherein the reference and/or test elements are arranged.

23. An apparatus for the electromagnetic spectrum or optical analysis of a material to be analyzed that is located in a product space for the photometric, spectrophotometric or image analysis of powder, bulk material, and granules, with a measuring probe which is arranged in a housing, with at least one radiation or light measuring element, a measuring window which is arranged in a path of rays in a wall of the housing, and with at least one detection element for the analysis, the measuring probe being formed and guided displaceably in an axial direction in such a way that at least part of the housing in which the measuring window is located enters through an opening into the product space in which the material to be analyzed is located, for the analysis, wherein at least one measuring window is arranged in at least one subregion of a circumferential wall of the housing, and that the same measuring window is used in reflection for the detection element, and in that a sealing cap is located between a front end face of the housing and the measuring window arranged in the circumferential wall, which sealing cap is at least partially still in the region of the opening in the product space, and consequently covers the opening, in a retracted position of the measuring probe in which the measuring window is outside the product space, wherein at least one beam deflecting device is arranged in the region of the measuring window in the interior of the housing, arranged in such a way that axially incident light or radiation can be deflected at least approximately into a radial direction to the at least one measuring window in the circumferential wall of the housing.

24. The apparatus as claimed in claim 23, wherein at least one mirror is provided as the beam deflecting device.

25. The apparatus as claimed in claim 24, wherein a number of mirrors arranged distributed over the circumference are provided.

26. The apparatus as claimed in claim 25, wherein the at least one mirror has at least approximately the form of a pyramid or cone with a number of mirrors surfaces.

27. The apparatus as claimed in claim 26, wherein the beam deflecting device is formed such that it can be turned or pivoted.

28. A method for the electromagnetic spectrum or optical analysis of a material to be analyzed that is located in a product space for the photometric, spectrophotometric or image analysis of powder, bulk material, and granules, with a measuring probe which is arranged in a housing, with at least one radiation or light measuring element, with at least one measuring window which is arranged in a path of rays in a wall of the housing, and with at least one detection element for the analysis, the measuring probe being arranged in a guide and entering through an opening into the interior of the product space in which the material to be analyzed is located, after which measurements are carried out through the measuring window, wherein the measurement is carried out through the at least one measuring window arranged in at least one subregion of a circumferential wall of the housing, and that the same measuring window is used in reflection for the detection element, after which the measuring probe is retracted from the opening of the container to the extent that the measuring window is outside the product space in a cleaning position, wherein measurements are carried out at different depths of entry of the measuring probe in the interior of the product space and that for cleaning at least the measuring window of the measuring probe, cleaning medium is introduced into an intermediate space between the guide and the housing of the measuring probe by at least one inflow and outflowed by at least one outflow.

29. The method as claimed in claim 28, wherein, with a partial retraction of the measuring probe from the product space, the housing of the measuring probe is guided past a scraper ring as a sealing part.

30. The method as claimed in claim 29, wherein, for cleaning a sealing and/or the interior of the product space, the measuring probe is pushed into a position in which there is a connection between a flushing medium chamber and the product space.

31. The method as claimed in claim 28, wherein a calibration is carried out in the retracted position of the measuring probe.

32. The method as claimed in claim 28, wherein dry gas is introduced into the interior of a cylinder guide in the retracted position of the measuring probe.

33. The method as claimed in claim 32, wherein the gas pressure of the dry gas in the interior of a cylinder guide is monitored.

34. The method as claimed in claim 28, wherein measurements are performed in segmental regions through a number of measuring windows arranged distributed over the circumferential wall of the housing.

35. The method as claimed in claim 34, wherein different measuring methods are used in at least some of the segmental regions.

36. An apparatus for the electromagnetic spectrum or optical analysis of a material to be analyzed that is located in a product space for the photometric, spectrophotometric or image analysis of powder, bulk material, and granules, with a measuring probe which is arranged in a housing, with at least one radiation or light measuring element, a measuring window which is arranged in a path of rays in a wall of the housing, and with at least one detection element for the analysis, the measuring probe being formed and guided displaceably in a guide in an axial direction in such a way that at least part of the housing in which the measuring window is located enters through an opening into the product space in which the material to be analyzed is located, for the analysis, wherein at least one measuring window is arranged in at least one sub-region of a circumferential wall of the housing, and that the same measuring window is used in reflection for the detection element, and in that a sealing cap is located between a front end face of the housing and the measuring window arranged in the circumferential wall, which sealing cap is at least partially still in the region of the opening in the product space, and consequently covers the opening, in a retracted position of the measuring probe in which the measuring window is outside the product space, wherein reference and/or test elements are arranged in the guide and wherein at least one beam deflecting device is arranged in the region of the measuring window in the interior of the housing, arranged in such a way that axially incident light or radiation can be deflected at least approximately into a radial direction in the circumferential wall of the housing.

37. The apparatus as claimed in claim 36, wherein at least one mirror is provided as the at least one beam deflecting device.

38. The apparatus as claimed in claim 37, wherein a number of mirrors arranged distributed over a circumference are provided.

39. The apparatus as claimed in claim 38, wherein the at least one mirror has at least approximately the form of a pyramid or cone with a number of mirrors surfaces.

40. The apparatus as claimed in claim 36, wherein the at least one beam deflecting device is formed such that it can be turned or pivoted.

41. An apparatus for the electromagnetic spectrum or optical analysis of a material to be analyzed that is located in a product space for the photometric, spectrophotometric or image analysis of powder, bulk material, and granules, with a measuring probe which is arranged in a housing, with at least one radiation or light measuring element, a measuring window which is arranged in a path of rays in a wall of the housing, and with at least one detection element for the analysis, the measuring probe being formed and guided displaceably in a guide in an axial direction in such a way that at least part of the housing in which the measuring window is located enters through an opening into the product space in which the material to be analyzed is located, for the analysis, wherein at least one measuring window is arranged in at least one sub-region of a circumferential wall of the housing, and that the same measuring window is used in reflection for the detection element, and in that a sealing cap is located between a front end face of the housing and the measuring window arranged in the circumferential wall, which sealing cap is at least partially still in the region of the opening in the product space, and consequently covers the opening, in a retracted position of the measuring probe in which the measuring window is outside the product space, wherein reference and/or test elements are arranged in the guide and that a flushing device for cleaning at least the measuring window of the measuring probe in the retracted position of the measuring probe is provided, wherein the flushing device has a flushing medium chamber, which is arranged in an intermediate space between the housing and the guide at least in the region of the measuring window, the flushing medium chamber being provided with at least one inflow and at least one outflow for flushing medium and wherein at least one beam deflecting device is arranged in the region of the measuring window in the interior of the housing, arranged in such a way that axially incident light or radiation can be deflected at least approximately into a radial direction to the measuring window in the circumferential wall of the housing.

42. The apparatus as claimed in claim 41, wherein at least one mirror is provided as the at least one beam deflecting device.

43. The apparatus as claimed in claim 42, wherein a number of mirrors arranged distributed over a circumference are provided.

44. The apparatus as claimed in claim 43, wherein the at least one mirror has at least approximately the form of a pyramid or cone with a number of mirrors surfaces.

45. The apparatus as claimed in claim 41, wherein the at least one beam deflecting device is formed such that it can be turned or pivoted.

46. An apparatus for the electromagnetic spectrum or optical analysis of a material to be analyzed that is located in a product space for the photometric, spectrophotometric or image analysis of powder, bulk material, and granules, with a measuring probe which is arranged in a housing, with at least one radiation or light measuring element, a measuring window which is arranged in a path of rays in a wall of the housing, and with at least one detection element for the analysis, the measuring probe being formed and guided displaceably in an axial direction in such a way that at least part of the housing in which the measuring window is located enters through an opening into the product space in which the material to be analyzed is located, for the analysis, wherein at least one measuring window is arranged in at least one subregion of a circumferential wall of the housing, and that the same measuring window is used in reflection for the detection element, and in that a sealing cap is located between a front end face of the housing and the measuring window arranged in the circumferential wall, which sealing cap is at least partially still in the region of the opening in the product space, and consequently covers the opening, in a retracted position of the measuring probe in which the measuring window is outside the product space, wherein a flushing device for cleaning at least the measuring window of the measuring probe in the retracted position of the measuring probe is provided, which has a flushing medium chamber, which is arranged in an intermediate space between the housing and the guide at least in the region of the measuring window, the flushing medium chamber being provided with at least one inflow and at least one outflow for flushing medium and wherein at least one beam deflecting device is arranged in the region of the measuring window in the interior of the housing, arranged in such a way that axially incident light or radiation can be deflected at least approximately into a radial direction to the measuring window in the circumferential wall of the housing.

47. The apparatus as claimed in claim 46, wherein at least one mirror is provided as the at least one beam deflecting device.

48. The apparatus as claimed in claim 47, wherein a number of mirrors arranged distributed over the circumference are provided.

49. The apparatus as claimed in claim 48, wherein the at least one mirror has at least approximately the form of a pyramid or cone with a number of mirrors surfaces.

50. The apparatus as claimed in claim 46, wherein the at least one beam deflecting device is formed such that it can be turned or pivoted.

* * * * *

UNITED STATES PATENT AND TRADEMARK OFFICE
CERTIFICATE OF CORRECTION

| | | |
|---|---|---|
| PATENT NO. | : 7,869,028 B2 | |
| APPLICATION NO. | : 11/995403 | |
| DATED | : January 11, 2011 | |
| INVENTOR(S) | : Mannhardt et al. | |

It is certified that error appears in the above-identified patent and that said Letters Patent is hereby corrected as shown below:

Column 2, line 14, "2-0" should be deleted

Column 5, line 28, "3600" should be "360°"

Signed and Sealed this
Fifteenth Day of March, 2011

David J. Kappos
*Director of the United States Patent and Trademark Office*